US00PP13233P2

(12) United States Plant Patent
de Koning

(10) Patent No.: US PP13,233 P2
(45) Date of Patent: Nov. 12, 2002

(54) MELITTIS PLANT NAMED 'ROYAL VELVET DISTINCTION'

(75) Inventor: Eleonore de Koning, Oudelande (NL)

(73) Assignee: Future Plants V.O.F., Lisserbroek (NL)

( * ) Notice: Subject to any disclaimer, the term of this patent is extended or adjusted under 35 U.S.C. 154(b) by 22 days.

(21) Appl. No.: 09/921,488

(22) Filed: Aug. 6, 2001

(51) Int. Cl.[7] ..... A01H 5/00
(52) U.S. Cl. ..... Plt./263
(58) Field of Search ..... Plt./263

*Primary Examiner*—Kent L. Bell
(74) *Attorney, Agent, or Firm*—C. A. Whealy

(57) ABSTRACT

A distinct cultivar of Melittis plant named 'Royal Velvet Distinction', characterized by its upright growth habit; relatively compact plant habit; and large purple and white bi-colored flowers.

2 Drawing Sheets

BOTANICAL CLASSIFICATION/CULTIVAR DESIGNATION

*Melittis melissophyllum* cultivar 'Royal Velvet Distinction'.

BACKGROUND OF THE INVENTION

The present Invention relates to a new and distinct cultivar of Melittis plant, botanically known as *Melittis melissophyllum*, and hereinafter referred to by the cultivar name 'Royal Velvet Distinction'.

The new Melittis originated from a cross-pollination of two unidentified selections of *Melittis melissophyllum*, not patented. The new Melittis was discovered as a single plant within the progeny of the cross-pollination by the Inventor in 1996 in Oudelande, The Netherlands. Plants of the new Melittis are more compact, have larger flowers and differ from plants of the unidentified parental selections in flower color.

Asexual reproduction of the new cultivar by divisions in Oudelande, The Netherlands since 1996, has shown that the unique features of this new Melittis are stable and reproduced true to type in successive generations.

SUMMARY OF THE INVENTION

Plants of the cultivar 'Royal Velvet Distinction' have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Royal Velvet Distinction'. These characteristics in combination distinguish 'Royal Velvet Distinction' as a new and distinct cultivar:

1. Upright growth habit.
2. Relatively compact plant habit.
3. Large purple and white bi-colored flowers.

In side-by-side comparisons conducted by the Inventor in Oudelande, The Netherlands, plants of the new Melittis are more compact and have larger flowers than plants of other unidentified selections of *Melittis melissophyllum*, not patented. In addition, plants of the new Melittis have purple and white bi-colored flowers whereas plants of the unidentified selection of *Melittis melissophyllum* have light pink-colored flowers.

BRIEF DESCRIPTION OF THE PHOTOGRAPHS

The accompanying colored photographs illustrate the overall appearance of the new Melittis, showing the colors as true as it is reasonably possible to obtain in colored reproductions of this type. Colors in the photographs may differ slightly from the color values cited in the detailed botanical description which accurately describe the colors of the new Melittis.

The photograph on the first sheet comprises a side perspective view of a typical 20-week old flowering plant of 'Royal Velvet Distinction' grown in a container under outdoor nursery conditions.

The photograph at the top of the second sheet is a close-up view of typical flowers of 'Royal Velvet Distinction'.

The photograph at the bottom of the second sheet is a close-up view of typical leaves of 'Royal Velvet Distinction'.

DETAILED BOTANICAL DESCRIPTION

In the following description, color references are made to The Royal Horticultural Society Colour Chart except where general terms of ordinary dictionary significance are used. Plants used for the following description were about one year old and grown under outdoor nursery conditions which closely approximate commercial production conditions during the spring and summer in Lisserbroek, The Netherlands.

Parentage: Cross-pollination of two unidentified selections of *Melittis melissophyllum*, not patented.

Propagation:

*Type cutting.*—By divisions.

*Time to initiate roots.*—About 21 days at 18° C.

*Root description.*—Fine, dark brown in color.

Plant description:

*Form.*—Perennial flowering plant; upright growth habit, inverted triangle. Relatively compact plant habit; appropriate for 1.5-liter or smaller containers.

*Crop time.*—After rooting, about 20 weeks are required to produce finished flowering plants in 1.5-liter containers.

*Plant height.*—About 40 cm.

*Plant diameter.*—About 25 cm.

*Vigor.*—Moderate to vigorous.

*Stem description.*—Main (basal) stems develop from the roots, typically about three to four per plant. Non-branching, lateral branches typically do not develop. Length: About 40 cm. Diameter: About 3.5 mm. Internode length: About 5.5 cm. Cross-section: Square. Strength: Strong. Texture: Pubescent. Fragrance: When rubbed, lemon-like scent. Color: 145A to 145B.

*Foliage description.*—Leaves opposite, single, generally symmetrical, and long-persisting. Length: About 8 cm. Width: About 5 cm. Shape: Elliptic; apex, acute; base, attenuate. Margin: Crenate to serrate. Texture, upper and lower surfaces: Pubescent; slightly rugose. Fragrance: When rubbed, lemon-like scent. Venation pattern: Pinnate. Petiole: Length: About 1.8 cm. Diameter: About 2 mm. Color: Young and mature foliage, upper surface: 137B to 146A. Young and mature foliage, lower surface: 138A. Venation, upper surface: 137B to 146A. Venation, lower surface: 145A. Petiole: 145A.

Flower description:

*Appearance.*—Single bilabiate flowers with two fused petals, an upper lip and a lower lip with two lateral lobes; flowers arranged in axillary whorls, about six flowers per whorl. Flowers not persistent.

*Natural flowering season.*—July through September in the Netherlands; flowering continuous.

*Fragrance.*—When rubbed, lemon-like scent.

*Flower size.*—Height (length): About 3.5 cm. Width: About 2.5 cm.

*Flower buds.*—Length: About 1.5 cm. Diameter: About 9 mm. Shape: Obovate. Color: Initially 154D to 1D with development.

*Petals.*—Length: Upper lip: About 3.6 cm. Lower lip: About 4 cm. Width: Upper lip: About 1.4 cm. Lower lip: About 1.5 cm; with lateral lobes, about 2.5 cm. Shape: Upper lip: Orbicular. Lower lip: Spatulate. Lateral lobes: Broadly obovate to orbicular. Apex: Rounded. Margin: Upper lip: Entire. Lower lip: Crenate. Lateral lobes: Entire. Texture: Upper surface: Smooth. Lower surface: Rough, pubescent. Color: When opening, upper surface: Upper lip: 155C. Lower lip: 72B. Lateral lobes: 155C. When opening, lower surface: Upper lip: 155C. Lower lip: 155C underlain with 72B. Lateral lobes: 155C. Fully opened, upper surface: Upper lip: 155C. Lower lip: 70A; throat, alternating stripes of 155C and 70A; narrow margin, 155C. Lateral lobes: 155C. Fully opened, lower surface: Upper lip: 155C. Lower lip: 155C underlain with 70A. Lateral lobes: 155C.

*Sepals.*—Quantity: Three. Calyx length: About 1.5 cm. Calyx diameter: About 1 cm. Calyx shape: Campanulate. Sepal shape: Ovate to elliptic. Sepal apex: Acute. Sepal margin: Entire. Texture, upper and lower surfaces: Densely pubescent. Color: Upper surface: 144B. Lower surface: 143A.

*Peduncle.*—Length: About 5 mm. Diameter: About 1 mm. Angle: About 60 to 85° from vertical. Strength: Strong. Texture: Smooth. Color: 143A.

*Reproductive organs.*—Stamens: Quantity: Four per flower. Anther shape: Roughly reniform. Anther length: About 1.5 mm. Anther color: 155C. Pollen amount: Moderate. Pollen color: 155A. Pistils: Quantity: One per flower. Pistil length: About 3 cm. Style color: 155A. Stigma length: About 0.4 mm. Stigma color: 155A. Ovary color: 150D.

*Seed description.*—Length: About 2.5 mm. Diameter: About 2.5 mm. Color: 200A.

*Fruit description.*—Length: About 6 mm. Diameter: About 5 mm. Color: 200B to 200C, 200A with development.

Disease resistance: Plants of the new Melittis have not been noted to be resistant to pathogens common to Melittis.

Temperature tolerance: Plants of the new Melittis are tolerant to temperatures from 15 to 35° C.

It is claimed:

1. A new and distinct cultivar of Melittis plant named 'Royal Velvet Distinction', as illustrated and described.

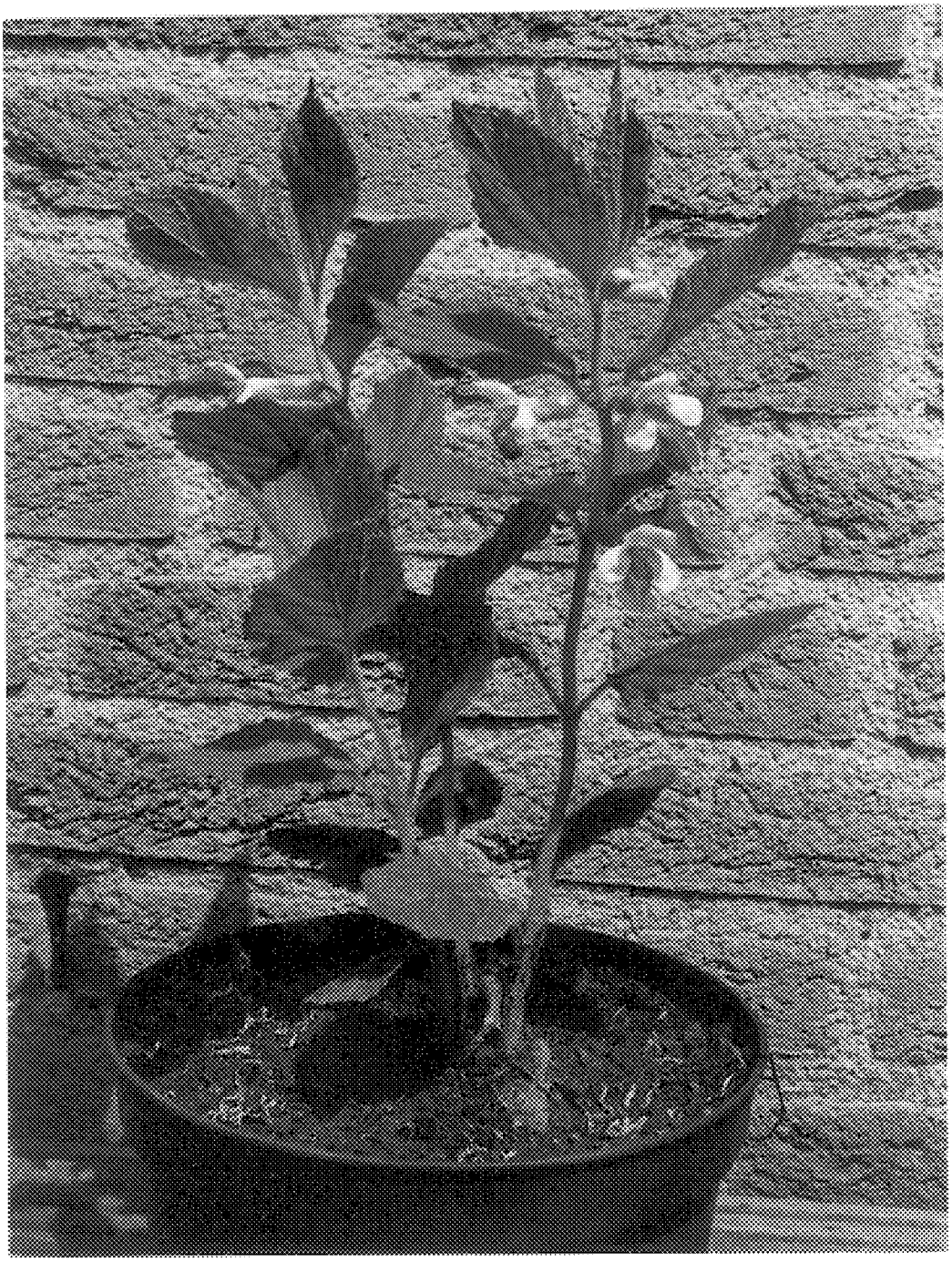

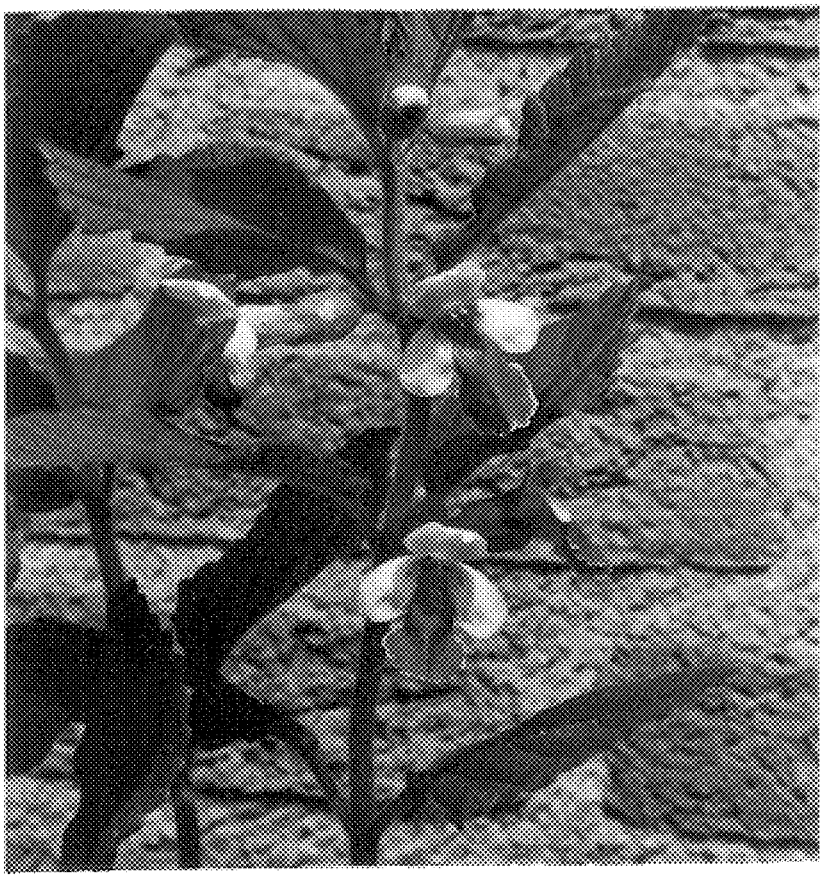
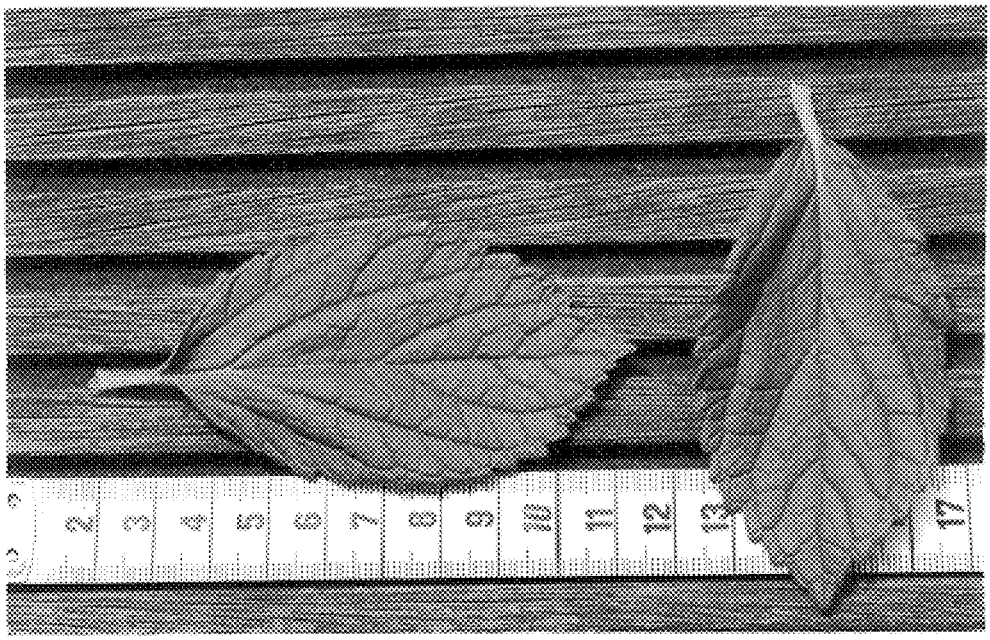

* * * * *